United States Patent

Dupelle et al.

[11] Patent Number: 6,019,877
[45] Date of Patent: Feb. 1, 2000

[54] PROTECTING MEDICAL ELECTRODES FROM CORROSION

[75] Inventors: Michael R. Dupelle, North Attleboro; Deborah T. Jones, Dartmouth, both of Mass.; Carolyn L. Schmiedeknecht, West Warwick, R.I.; Sheldon S. White, Brookline, Mass.

[73] Assignee: ZMD Corporation, Wilmington, Del.

[21] Appl. No.: 09/099,256

[22] Filed: Jun. 18, 1998

[51] Int. Cl.[7] ..................................... C23F 13/00
[52] U.S. Cl. ............... 204/196.11; 204/196.12; 204/196.23; 204/196.25; 204/196.26; 600/372; 600/391; 600/396; 600/397; 607/142; 607/149; 607/152
[58] Field of Search .......... 204/196.11, 196.12, 204/196.23, 196.25, 196.26; 600/391, 396, 397, 372; 607/142, 149, 152

[56] References Cited

U.S. PATENT DOCUMENTS

| | | | |
|---|---|---|---|
| 4,554,924 | 11/1985 | Engel | 600/397 |
| 4,727,881 | 3/1988 | Craighead et al. | 600/397 |
| 4,777,954 | 10/1988 | Keusch et al. | 607/152 |
| 4,846,185 | 7/1989 | Carim | 600/391 |
| 5,566,672 | 10/1996 | Faasse, Jr. | 607/149 |
| 5,779,632 | 7/1998 | Dietz et al. | 600/391 |

OTHER PUBLICATIONS

The International Nickel Company, Inc.; "Corrosion in Action"; 67 Wall Street, New York, New York 10005; pp. 1–47; 1961 no month available.

Mahan, Bruce H.; *University Chemistry*, Third Edition; Addison–Wesley Publishing Company; pp. 289–291; 1975 no month available.

*Primary Examiner*—Bruce F. Bell
*Attorney, Agent, or Firm*—Fish & Richardson, PC

[57] ABSTRACT

A medical electrode assembly includes an electrically conductive electrode, an electrically conductive sacrificial element, and a layer of electrically conductive gel. The electrode has an electrical terminal to connect with external electrical circuitry. The sacrificial element is electrically connected with the electrode through an impedance element or a power supply. The layer of electrically conductive gel contacts both the electrode and the sacrificial element so as to form an anode-cathode cell in which the sacrificial element functions as a sacrificial anode that corrodes and the electrode functions as a cathode that is protected from corrosion.

37 Claims, 2 Drawing Sheets

PROTECTING MEDICAL ELECTRODES FROM CORROSION

BACKGROUND OF THE INVENTION

This invention relates to medical electrode assemblies and techniques for protecting medical electrodes from corrosion.

Medical electrode assemblies for use in procedures such as defibrillation typically include an electrode formed of metal, or formed of a conductive ink printed on a substrate, and a liquid or solid electrically conductive gel covering the electrode so that electrical current from the electrode passes through the gel to a patient's body rather than directly from the electrode to the patient.

SUMMARY OF THE INVENTION

One aspect of the invention features a medical electrode assembly that includes an electrically conductive electrode, an electrically conductive sacrificial element, and a layer of electrically conductive gel. The electrode has an electrical terminal to connect with external electrical circuitry. An electrical conductor electrically connects the sacrificial element with the electrode. The layer of electrically conductive gel contacts both the electrode and the sacrificial element so as to form an anode-cathode cell in which the sacrificial element functions as a sacrificial anode that corrodes and the electrode functions as a cathode that is protected from corrosion.

The invention provides protection against corrosion that can naturally occur due to small variations in energy levels across small distances on the surface of a gel-covered electrode. For example, if there is a small air bubble between an electrode and an electrically conductive gel, the energy level of metal ions within the bubble could tend to be different from the energy level of metal ions immediately outside of the bubble. Also, there can be slight differences in the composition of the electrode metal or ink, or in the composition of the gel, from one location to an adjacent location. Any of these conditions can result in an energy level at one location on the electrode being slightly different than an energy level at an immediately adjacent location. High-energy locations function as anodes of small corrosive electrolytic cells.

By providing a sacrificial element, the invention protects against such corrosion of the electrode by causing the entire electrode to function as a cathode and causing the entire sacrificial element to function as an anode that corrodes. The electrode is protected by cathodic protection until the sacrificial element is consumed by corrosion.

The sacrificial element may be connected to the electrode through an electrical element selected in order to prolong an electrochemical reaction between the electrode and the sacrificial element. The electrical element, which may be, for example, a resistor and/or a power supply selected based on the measured potential difference, provides additional shelf life for the sacrificial element by slowing down the reaction between the electrode and the sacrificial element and thereby allowing use of the sacrificial element for a long period of time before the sacrificial element is consumed, which ends the protection period.

Other features and advantages of the invention will be apparent from the following detailed description, drawings, and claims.

DETAILED DESCRIPTION

Figure 1:
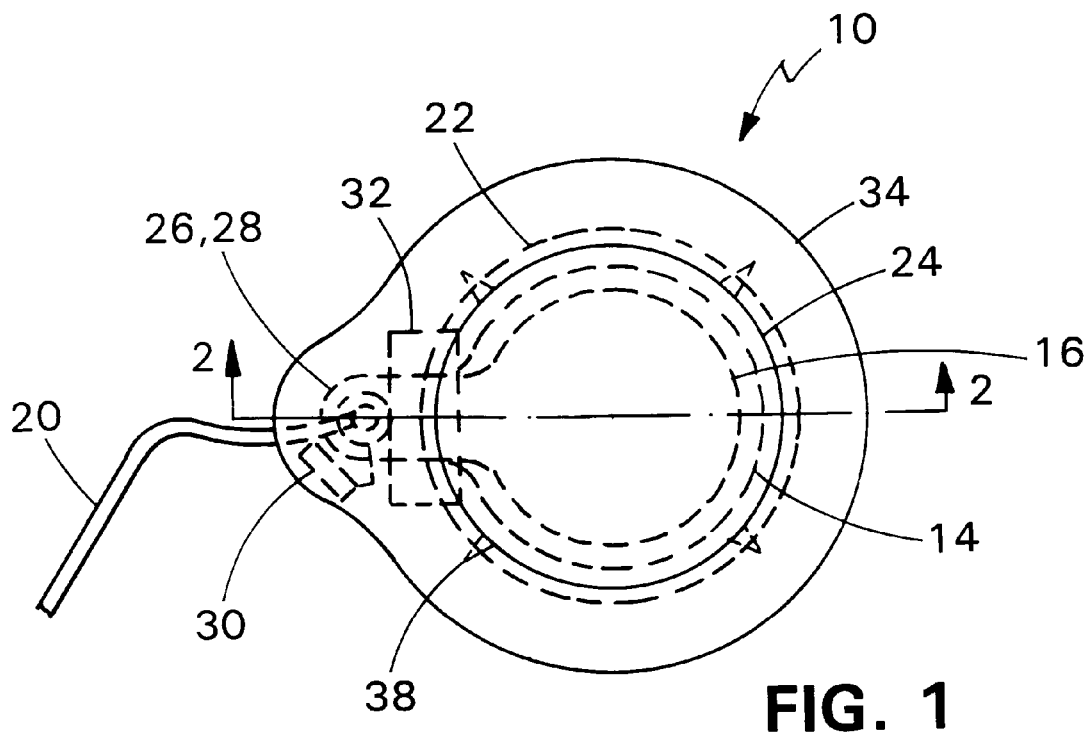
FIG. 1 is a top view of an electrode assembly according to the invention.
Figure 2:
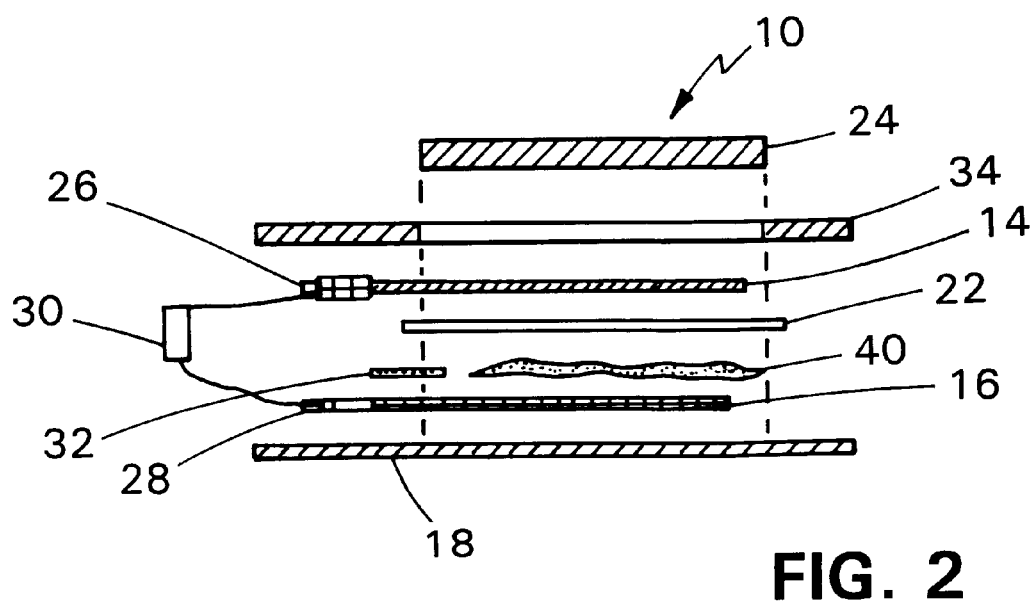
FIG. 2 is an exploded, cross-sectional view of the components of the electrode assembly of FIG. 1, taken along line 2—2 in FIG. 1.

With reference to FIGS. 1 and 2, an electrode assembly 10 with extended shelf life for transcutaneously delivering defibrillation pulses to a patient'heart includes a disk-shaped electrode 14, formed of tin, and a disk-shaped sacrificial element 16, formed of aluminum, positioned beneath electrode 14. Sacrificial element 16 is separated from electrode 14 by a non-conductive filter 22 everywhere except at tabs 26 and 28 of the electrode and the sacrificial element respectively. Tabs 26 and 28 of the electrode and sacrificial element are electrically connected with each other, either directly by crimping or soldering, or through a resistor 30. Tab 26 of electrode 14 is connected to copper electrical wire 20 through an electrical terminal in order to connect with an external source of electric current.

A foam or sponge layer 24 saturated with liquid electrically conductive gel covers the entire top surface of electrode 14, except for extension tab 26. Foam layer 24 fits within a circular gel well defined by a foam frame 34. The dashed lines in FIG. 2 indicate the relative alignment of various structures of the electrode assembly with the edge of the gel well. An insulating foam substrate 18 has a perimeter identical to that of foam frame 34, and inner surfaces of foam substrate 18 and foam frame 34 adhere to each other through adhesive in order to hold the various layers of electrode assembly 10 together. Foam layer 24 has tabs 38 that are captured by adhesive in-between foam frame 34 and foam substrate 18 in order to hold foam layer 24 in place. A second electrically conductive gel layer 40 covers the entire top surface of sacrificial element 16, except for tab 28. Gel layer 40 contacts electrode 14 as well as sacrificial element 16 in order to form a complete electrical circuit between electrode 14 and sacrificial element 16. Gel layer 40 is also in physical and electrical contact with the gel within foam layer 24 (through filter 22 around the perimeter of electrode 14 except at the location of tab 26).

Sacrificial element 16 and electrode 14 form, through electrically conductive gel layer 40, an anode-cathode cell that protects electrode 14 from corrosion by the principle of cathodic protection and extends the shelf life of electrode 14. The sacrificial element (which may be, for example, aluminum) tends to go into solution more readily than the electrode (which may be, for example, tin), assuming contact of the aluminum and tin with the electrically conductive gel. As soon as a small portion of the aluminum goes into solution the aluminum becomes an anode, the tin becomes a cathode, and the cathode is protected by cathodic protection until the aluminum is consumed. In order for the electrochemical reaction to work, a continuous mass of gel contacts surfaces of both the electrode and the sacrificial element.

Resistor 30 provides additional shelf life for sacrificial element 16 by slowing down the reaction between the two metals and allowing use of the aluminum for a longer period of time before the aluminum is finally consumed, which ends the protection period. If the resistance of resistor 30 is too high, however, then the reduced electrical current through the resistor will cause the aluminum to have less tendency to go into solution and to function less as an anode, and will result in the tin having a tendency to go into solution. Of course, if there is not a complete circuit from the aluminum through the gel to the tin and then back to the aluminum or vice versa (a theoretical infinite resistance of resistor 30), then the tin and aluminum will corrode at whatever rate they would normally corrode, independently of each other, because there is no cathode or anode.

The appropriate resistance of resistor 30 can be determined by measuring the electrical potential difference between the tin and the aluminum with the gel in the circuit. However, if the composition of the gel is changed, for example, it would be necessary to measure the electrical potential difference again and then recalculate the appropriate resistance value for resistor 30, assuming that the measured electrical potential difference is changed, as would likely be the case. In one particular embodiment, the resistance of resistor 30 can be up to about 680 kilo-ohms, but not as high as 1000 kilo-ohms, in order to slow the electrochemical reaction down to provide protection over long periods of time.

Techniques for increasing the duration of the cathodic protection period include not only the use of an appropriate resistor 30, but also increasing the surface area of the aluminum, increasing the thickness of the aluminum, and any combination of these techniques. Increasing the thickness of the aluminum could result in the electrode assembly being too stiff to conform to a typical body contour, however.

In general, whatever metal forms electrode 14, in this case tin, should be protected with a sacrificial element 16 of a metal, in this case aluminum, that is more active than (i.e., has a tendency to go into solution more readily than) the metal of electrode 14. For example, sacrificial element 16 could be made of zinc instead of aluminum, or could be made of any material that is more active than and therefore corrodes faster than the material of electrode 14. If the metal of sacrificial element 16 has an activity or potential to go into solution that is greater than but very close to that of electrode 14, then the cathodic protection effect is somewhat reduced but the duration of the protection period will tend to be relatively long. Sacrificial element 16 could even be manufactured from the same material as that of electrode 14 or a material that is less active than the material of electrode 14 if a power supply such as a battery is connected between electrode 14 and sacrificial element 16 in order to drive the voltage potential in a direction reverse from that which normally occurs when the electrode is coupled to a less active sacrificial element. The power supply could be selected based on the potential difference between electrode 14 and sacrificial element 16, measured through the electrically conductive gel. In other embodiments one or both of electrode 14 and sacrificial element 16, instead of being formed of a sheet of metal, could be formed of a substrate printed with a conductive ink such as a silver and silver chloride ink.

Foam frame 34 forms a disk-shaped gel well within which electrode 14 and sacrificial element 16 are located (except for the tabs 26 and 28, which extend out beyond the edge of the gel well). Foam layer 24 fits into the gel well on top of electrode 14. The top surface of foam frame 34 includes an adhesive that adheres to a patient's body when the electrode assembly is applied to the patient's body. Foam layer 24 extends slightly above (about $1/16$ inch) foam frame 34, so that when the electrode assembly is applied to a patient's body, foam layer 24 experiences compression and the physician can be sure that gel is in good contact with the patient's skin all the way across the gel well region of the electrode assembly. A styrene protective cover (not shown) fits over foam layer 24 while the electrode assembly is in storage. The styrene protective cover includes a bubble that accommodates the protrusion of foam layer 24 above the rest of the electrode assembly while the styrene protective cover prevents the gel from smearing.

A fine filter 22 made of fiberglass or other filter material is positioned between sacrificial element 16 and electrode 14. Filter 22 covers sacrificial element 16 and extends under electrode 14, and maintains constant spacing between the electrode 14 and sacrificial element 16 so that they do not contact each other and so that the distance between electrode 14 and sacrificial element 16, and thus the thickness of the gel between the electrode and the sacrificial element, is constant as a function of location. A variation in the thickness of the gel as a function of location could result in wide variations in the rate of corrosion of sacrificial element 16 as a function of location. Filter 22 ensures that corrosion progresses at essentially the same rate everywhere.

Filter 22 also keeps corrosion byproducts from moving to undesired locations through the electrically conductive gel, which in the embodiment of FIGS. 1 and 2 is in liquid form. In particular, filter 22 traps the byproducts, such as whitish hydroxides, that form during the corrosion process and might otherwise tend to seep into foam layer 24 and into plain view, which could lead a user to mistakenly conclude that there is something wrong with the electrode assembly. The liquid electrically conductive gel, however, can pass through filter 22 so that the electrochemical reaction can continue. Filter 22 need only be fine enough to block the corrosion byproducts, which tend to clump together.

A gel stopper in the form of a strip of double-sided insulating tape 32 is positioned between electrode 14 and sacrificial element 16 in the region of tabs 26 and 28, in order to hold filter 22 in place and in order to prevent any migration of the gel out of the gel field and into the region of tabs 26 and 28, resistor 30, copper wire 20, and the grommets that attach electrode 14 to wire 20 or to sacrificial element 16. Any such migration of gel could cause corrosion of these metal elements. Foam frame 34, which can be, for example, $1/8$ inch thick, covers the region of tabs 26 and 28 as well as the rest of the perimeter of electrode assembly 10, and the inner surface of foam frame 34 adheres to the top surface of electrode 14 to prevent migration of gel into the region of tab 26. Similarly, the inner surface of insulating foam substrate 18, which can be, for example, $1/16$ inch thick, adheres to the bottom surface of sacrificial element 16 to prevent migration of gel into the region of tab 28.

In alternative embodiments a solid electrically conductive gel may be employed rather than a liquid electrically conductive gel. Solid electrically conductive gel is typically more convenient for the physician or clinician than liquid electrically conductive gel in that solid electrically conductive gel does not readily flow. It is typically messy to clean up a patient after use of a liquid electrically conductive gel.

If a solid electrically conductive gel is employed, filter 22 and foam layer 24 are not required. Rather, a layer of solid electrically conductive gel would be placed within the disk-shaped gel well defined by foam frame 34. Because electrode 14 has a diameter slightly greater than that of sacrificial element 16, electrode 14 conceals sacrificial element 16 even though foam layer 24 is absent, and therefore conceals any color change of sacrificial element 16 due to corrosion. A visually perceptible corrosion or color change could lead a user to mistakenly conclude that there is something wrong with the electrode assembly.

The disk-shaped electrode assembly shown in FIGS. 1 and 2 is designed to be placed on the chest of a patient. A rectangular electrode assembly, designed to be placed on the back of the patient or a different location on the patient's chest, would have the same basic construction and dimensions as the electrode assembly shown in FIGS. 1 and 2, although a rectangular configuration could have a rectangular-shaped electrode and a rectangular-shaped sacrificial element rather than the disk-shaped electrode and sacrificial element 14 and 16 of FIGS. 1 and 2. A rectangular configuration should include more sacrificial metal in the corner regions than in non-corner regions, because corrosion tends to concentrate at these locations and therefore more sacrificial metal is required for cathodic protection. The electrode and sacrificial element may alternatively be shaped as ovals, long rectangular strips, U-shapes, rings, and numerous other possible configurations.

Figure 3:
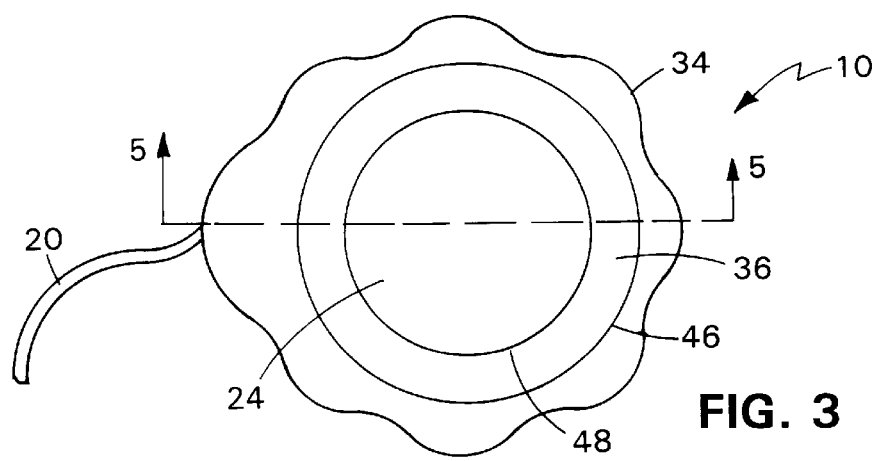
FIG. 3 is a top view of an alternate electrode assembly.
Figure 4:
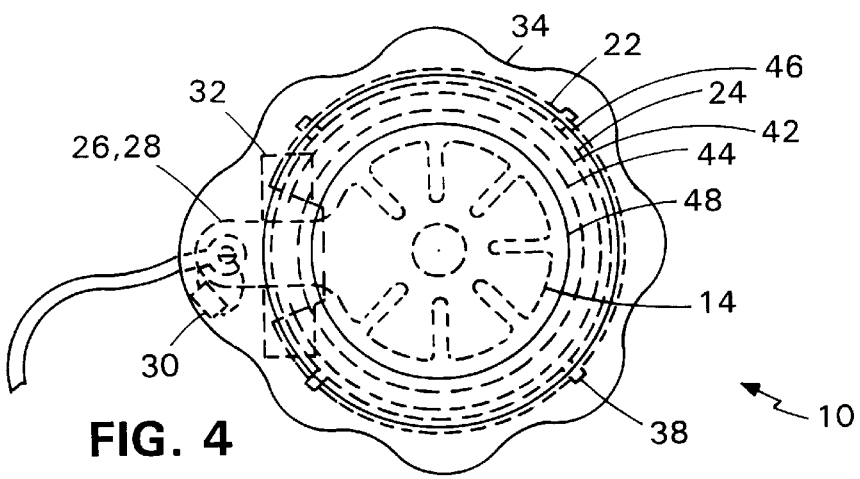
FIG. 4 is a top view of the electrode assembly of FIG. 3 showing, in phantom, the locations of various internal structures of the electrode assembly.
Figure 5:
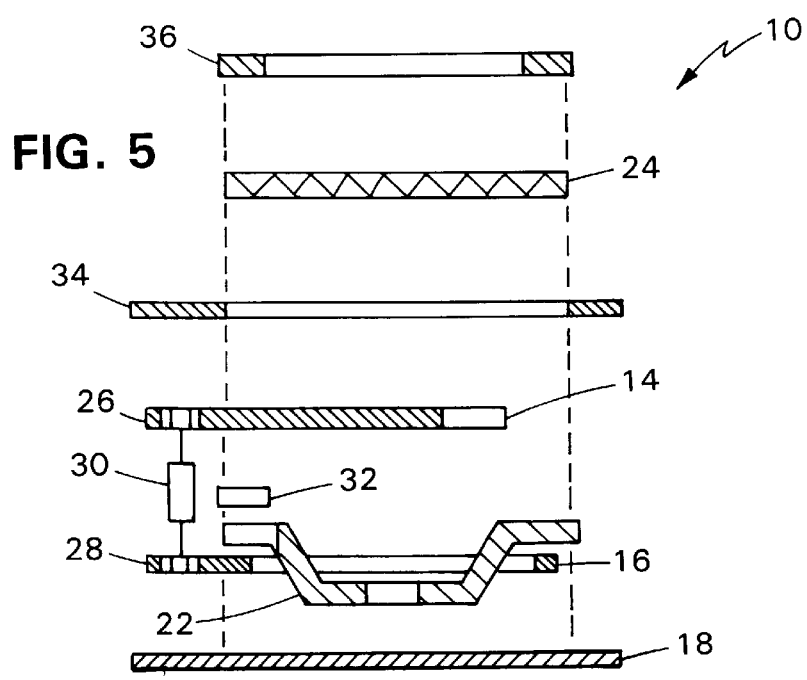
FIG. 5 is an exploded, cross-sectional view of the components of the electrode assembly of FIG. 3, taken along line 5—5 in FIG. 3.

With reference to FIGS. 3–5, another embodiment of an electrode assembly with extended shelf life is shown, in which structures analogous to those shown in FIGS. 1 and 2 are numbered identically. This electrode assembly employs a sacrificial ring 16 formed of aluminum, rather than a disk. The outer edge 42 and the inner edge 44 of sacrificial ring 16 are marked in FIG. 4. Sacrificial ring 16 is positioned beyond the perimeter of the electrode 14 but is separated from electrode 14 everywhere except at tabs 26 and 28 of the electrode and the sacrificial element respectively. The embodiment of FIGS. 3–5 does not have as much aluminum surface area as the embodiment of FIGS. 1 and 2, and thus the embodiment of FIGS. 1 and 2 may provide longer cathodic protection time than the embodiment of FIGS. 3–5.

In general, skin burning and reddening typically tends to occur at the perimeter of an electrode, because a large portion the energy that passes through the electrode passes through the perimeter of the electrode, and creates what is known in the industry as an "edge effect." The extent of skin reddening or burning (anywhere from mild reddening of the skin to an actual burn with blisters) depends on factors such as an individual patient's skin and the number of defibrillation shocks that are delivered to the patient. Manufacturers of medical electrodes have theorized that a lengthening of the perimeter of an electrode can dilute that energy and in effect put the same amount of energy through a longer perimeter. Accordingly, in the embodiment of FIGS. 3–5, electrode 14 is not in the form of a disk but is instead in the form of a daisy flower-petal shape having long cut-outs that increase the length of the perimeter of electrode 14. The electrode in the embodiment of FIGS. 1 and 2 could similarly be modified to have a daisy flower-petal shape. Other shapes having lengthy perimeters are also possible.

In the embodiment of FIGS. 3–5, foam layer 24 saturated with liquid electrically conductive gel covers the entire top surfaces of electrode 14 and sacrificial ring 16, except for extension tabs 26 and 28 of electrode 14 and sacrificial ring 16. Sacrificial ring 16 and electrode 14 form, through the electrically conductive gel in foam layer 24, an anode-cathode cell that protects electrode 14 from corrosion. The dashed lines in FIG. 5 indicate the relative alignment of various structures of the electrode assembly with the edge of the gel well defined by foam frame 34.

Filter 22 covers sacrificial element 16 and extends under electrode 14. Filter 22 keeps corrosion byproducts from moving through the electrically conductive gel, which in the embodiment of FIGS. 3–5 is in liquid form.

Mylar, vinyl, or other plastic type mask 36 extends slightly beyond foam layer 24, extending just inward of the inner perimeter of sacrificial ring 16. The outer edge 46 and the inner edge 48 of mask 36 are marked in FIGS. 3 and 4. Mask 36 includes a dielectric that prevents current from passing from the sacrificial ring directly to the patient. The upper surface of mask 36 has an adhesive that adheres to a patient's body, in addition to the adhesive on foam frame 34, when the electrode assembly is applied to the patient's body.

In alternative embodiments, the electrical connection between electrode 14 and sacrificial ring 16 could be fusible, so that the electrical connection can be broken if the physician does not want energy to be delivered to sacrificial ring 16 during therapy.

If a solid electrically conductive gel is employed in the embodiment of FIGS. 3–5 rather than a liquid electrically conductive gel, then a layer of solid electrically conductive gel would be placed within the disk-shaped gel well defined by foam frame 34 and another layer of solid electrically conductive gel would be placed between electrode 14 and sacrificial element 16.

If a solid electrically conductive gel is employed in the embodiment of FIGS. 3–5, filter 22 and foam layer 24 are not required. Even though filter 22 and foam layer 24 are absent, mask 36, which is opaque, conceals any color change in sacrificial ring 16 due to corrosion. A visually perceptible corrosion or color change could lead a user to mistakenly conclude that there is something wrong with the electrode assembly. If a liquid electrically conductive gel is used in the embodiment of FIGS. 3–5, on the other hand, mask 36 does not perform any concealing function because foam layer 24 is present (although mask 36 does perform the other function of preventing current from passing from the sacrificial ring directly to the patient). No equivalent of mask 36 is required in the embodiment of FIGS. 1 and 2, regardless of whether liquid or solid electrically conductive gel is used, because electrode 14 entirely covers sacrificial element 16 and therefore conceals any color change of sacrificial element 16 due to corrosion.

In other embodiments, sacrificial element 16 and filter 22 in FIGS. 1 and 2 or in FIGS. 3–5 could be moved from the locations at which they are shown and could instead be mounted on a peel-away layer that could be peeled off of the top of foam frame 34 and foam layer 24. Sacrificial element 16 would be mounted directly on the peel-away layer, facing foam layer 24, and filter 22 would be mounted on the peel-away layer so as to be interposed between sacrificial element 16 and foam layer 24. When the electrode assembly is ready for use, the peel-away layer, together with sacrificial element 16 and filter 22, would be removed, and the gel within foam layer 24 would be exposed. Filter 22 would prevent the aluminum corrosive byproducts from attaching themselves to the gel within foam layer 24, and when the peel-away layer is removed from the electrode assembly the corrosion byproducts would remain with the strip and none would stay with the gel in foam layer 24. If the corrosion byproducts were to remain with the gel in foam layer 24, foam layer 24 would be discolored. Moreover, the corrosion byproducts, such as aluminum hydroxide, would create hot spots on the surface of the gel where the gel interfaces with the patient's skin, because the corrosion products would probably have a conductivity different from that of the surrounding gel.

Other embodiments are within the following claims. For example, although electrodes for defibrillation have been described, the principles of the invention can similarly be applied to other types of medical electrodes useful for pacing, sensing, grounding, etc.

What is claimed is:

1. A medical electrode assembly comprising:
   an electrically conductive medical electrode having an electrical contact point to connect with external electrical circuitry;
   an electrically conductive sacrificial element electrically connected with the electrode; and
   an electrically conductive material contacting both the electrode and the sacrificial element so as to form, an anode-cathode cell in which the sacrificial element functions as a sacrificial anode that corrodes and the electrode functions as a cathode that is protected from corrosion.

2. The medical electrode of claim 1 wherein the electrically conductive material contacting both the electrode and the sacrificial element covers at least a portion of a surface of the electrode so as to prevent contact between the electrode and a patient's body when the medical electrode assembly is placed on the patient's body.

3. The medical electrode of claim 1 wherein the electrically conductive material forms a first layer, and further comprising a second layer of electrically conductive material, distinct from the first layer of electrically conductive material contacting both the electrode and the sacrificial element, covering at least a portion of a surface of the electrode so as to prevent contact between the electrode and a patient's body when the medical electrode assembly is placed on the patient's body.

4. The medical electrode assembly of claim 1 wherein the external electrical circuitry comprises a source of electrical current for defibrillation.

5. The medical electrode assembly of claim 1 wherein the external electrical circuitry comprises a source of electrical current for pacing.

6. The medical electrode assembly of claim 1 wherein the external electrical circuitry is configured to sense signals received by the electrode.

7. The medical electrode assembly of claim 1 wherein at least one of the electrode and the sacrificial element comprises a nonmetal.

8. The medical electrode assembly of claim 1 wherein the electrode and the sacrificial element each comprise a metal.

9. The medical electrode assembly of claim 8 wherein the electrode comprises tin.

10. The medical electrode assembly of claim 8 wherein the sacrificial element comprises aluminum.

11. The medical electrode assembly of claim 1 wherein the electrode is a plate-shaped structure, and the sacrificial element is a plate-shaped structure mounted on an insulating substrate beneath the electrode.

12. The medical electrode assembly of claim 1 wherein the electrode is a plate-shaped structure and the sacrificial element is a ring-shaped structure surrounding the electrode.

13. The medical electrode assembly of claim 1 further comprising a filter separating the electrode from the sacrificial element.

14. The medical electrode assembly of claim 1 further comprising a structure that contains the electrically conductive material, covering at least a portion of a surface of the electrode.

15. The medical electrode assembly of claim 1 further comprising an electrical element through which the sacrificial element is electrically connected with the electrode, the electrical element being selected to control an anode-cathode reaction between the sacrificial element and the electrode.

16. The medical electrode assembly of claim 15 wherein the electrical element comprises an impedance element.

17. The medical electrode assembly of claim 15 wherein the electrical element comprises a power supply.

18. The medical electrode assembly of claim 15 wherein the electrical element is selected to control the anode-cathode reaction between the sacrificial element and the electrode by slowing down the anode-cathode reaction.

19. The medical electrode assembly of claim 1 further comprising a blocking structure positioned between the electrode and the sacrificial element near a location at which the electrode is electrically connected with the sacrificial element, the blocking structure being positioned so as to prevent migration towards this location of the electrically conductive material that contacts both the electrode and the sacrificial element.

20. The medical electrode assembly of claim 1 wherein the sacrificial element is masked from view by the electrode.

21. The medical electrode assembly of claim 1 wherein the sacrificial element is masked from view by a dielectric mask.

22. The medical electrode assembly of claim 1 wherein the sacrificial element is removable from the medical electrode assembly prior to use of the electrode for treatment of a patient.

23. The medical electrode assembly of claim 1 wherein the electrically conductive material is a gel.

24. The medical electrode assembly of claim 23 wherein the electrically conductive material is a solid gel.

25. The medical electrode assembly of claim 23 wherein the electrically conductive material is a liquid gel.

26. The medical electrode assembly of claim 1 wherein the sacrificial element and the electrode have different chemical compositions.

27. The medical electrode assembly of claim 1 wherein the sacrificial element and the electrode have the same chemical composition.

28. The medical electrode assembly of claim 1 comprising no more than a single electrode.

29. The medical electrode assembly of claim 1 comprising no more than a single sacrificial element.

30. The medical electrode assembly of claim 1 wherein the electrode has a plate-shaped structure.

31. The medical electrode assembly of claim 1 further comprising a filter positioned to block movement of corrosion byproducts.

32. The medical electrode assembly of claim 1 wherein the sacrificial element is masked from view.

33. A medical electrode assembly comprising:
   an insulating substrate;
   an electrically conductive medical electrode mounted on the insulating substrate and having an electrical contact point to connect with external electrical circuitry;
   an electrically conductive material covering at least a portion of a surface of the electrode so as to prevent contact between the electrode and a patient's body when the medical electrode assembly is placed on the patient's body;
   an electrically conductive sacrificial element mounted on the insulating substrate, the sacrificial element being masked from view;
   an electrical element through which the sacrificial element is electrically connected with the electrode, the electrical element being selected to slow down an anode-cathode reaction between the sacrificial element and the electrode;

an electrically conductive material contacting both the electrode and the sacrificial element so as to form, together with an electrical pathway through the electrical element, an anode-cathode cell in which the sacrificial element functions as a sacrificial anode that corrodes and the electrode functions as a cathode that is protected from corrosion;

a blocking structure positioned between the electrode and the sacrificial element near a location at which the electrode is electrically connected with the sacrificial element, the blocking structure being positioned so as to prevent migration towards this location of the electrically conductive material that contacts both the electrode and the sacrificial element.

34. A medical electrode comprising:

an electrically conductive medical electrode having an electrical terminal to connect with external electrical circuitry;

an electrically conductive sacrificial element;

an electrically conductive material contacting both the electrode and the sacrificial element; and an electrical element electrically connecting the electrode with the sacrificial element, selected in order to prolong an electrochemical reaction between the electrode and the sacrificial element, so as to form an anode-cathode cell in which the sacrificial element functions as a sacrificial anode that corrodes and the electrode functions as a cathode that is protected from corrosion.

35. The medical electrode of claim 33 wherein the electrical element comprises an impedance element.

36. The medical electrode of claim 34 wherein the impedance element comprises a resistor.

37. The medical electrode of claim 33 wherein the electrical element comprises a power supply.

* * * * *